United States Patent
Iftimia et al.

(10) Patent No.: US 11,109,759 B2
(45) Date of Patent: Sep. 7, 2021

(54) APPARATUS AND METHOD FOR ASSESSMENT OF INTERSTITIAL TISSUE

(71) Applicant: Physical Sciences, Inc., Andover, MA (US)

(72) Inventors: Nicusor V. Iftimia, Chelmsford, MA (US); Whanwook Chang, Fort Lee, NJ (US)

(73) Assignee: Physical Sciences, Inc., Andover, MA (US)

( * ) Notice: Subject to any disclaimer, the term of this patent is extended or adjusted under 35 U.S.C. 154(b) by 567 days.

(21) Appl. No.: 15/907,557

(22) Filed: Feb. 28, 2018

(65) Prior Publication Data
US 2018/0263498 A1    Sep. 20, 2018

Related U.S. Application Data

(62) Division of application No. 14/795,570, filed on Jul. 9, 2015, now abandoned.

(60) Provisional application No. 62/022,497, filed on Jul. 9, 2014.

(51) Int. Cl.
*A61B 5/00* (2006.01)
*A61B 5/06* (2006.01)

(52) U.S. Cl.
CPC .......... *A61B 5/0066* (2013.01); *A61B 5/0071* (2013.01); *A61B 5/0075* (2013.01); *A61B 5/0084* (2013.01); *A61B 5/065* (2013.01); *A61B 5/6848* (2013.01); *A61B 5/742* (2013.01)

(58) Field of Classification Search
CPC ... A61B 5/0066; A61B 5/0071; A61B 5/0075; A61B 5/0084; A61B 5/065; A61B 5/742; A61B 5/6848
See application file for complete search history.

(56) References Cited

U.S. PATENT DOCUMENTS

| | | | |
|---|---|---|---|
| 6,564,087 B1 | 5/2003 | Pitris et al. | |
| 7,848,791 B2* | 12/2010 | Schmitt | A61B 5/0066 356/497 |
| 2003/0045798 A1 | 3/2003 | Hular et al. | |
| 2005/0020925 A1* | 1/2005 | Kleen | A61B 5/0084 600/476 |
| 2006/0007316 A1* | 1/2006 | Yamanaka | G02B 7/102 348/207.99 |

(Continued)

OTHER PUBLICATIONS

Kawase, Yoshiaki, et al. "Comparison of nonuniform rotational distortion between mechanical IVUS and OCT using a phantom model," Ultrasound in Medicine and Biology vol. 33 No. 1 (2007); pp. 67-73.

(Continued)

*Primary Examiner* — Sean D Mattson
(74) *Attorney, Agent, or Firm* — Iandiorio Teska & Coleman, LLP (57) ABSTRACT

A handheld optical coherence tomography imaging and tissue sampling system and method of imaging and sampling a tissue is disclosed. The method includes inserting a catheter probe into a biopsy needle. The biopsy needle can be attached to a hand-held scanning and sampling device. The biopsy needle is maneuvered to an investigation site. A three-dimensional image of the tissue at the investigation site is captured with the catheter probe.

10 Claims, 6 Drawing Sheets

(56) References Cited

U.S. PATENT DOCUMENTS

| | | | |
|---|---|---|---|
| 2007/0106155 A1* | 5/2007 | Goodnow | A61B 8/12 600/437 |
| 2009/0192358 A1* | 7/2009 | Jaffer | G01N 21/4795 600/182 |
| 2009/0323076 A1 | 12/2009 | Li et al. | |
| 2010/0210937 A1* | 8/2010 | Tearney | A61B 5/0086 600/424 |
| 2012/0016316 A1 | 1/2012 | Zhuang et al. | |
| 2012/0116234 A1* | 5/2012 | Farcy | A61B 5/14556 600/478 |
| 2012/0307014 A1* | 12/2012 | Wang | G01B 9/02091 348/46 |

OTHER PUBLICATIONS

Wieser, Wolfgang, et al. "Multi-megahertz OCT: High quality 3D Imaging at 20 million A-scans and 4.5 GVoxels per second," Optics Express vol. 18 No. 14 (2010); pp. 14685-14704.

* cited by examiner

APPARATUS AND METHOD FOR ASSESSMENT OF INTERSTITIAL TISSUE

RELATED APPLICATIONS

This application is a divisional application of U.S. patent application Ser. No. 14/795,570 filed Jul. 9, 2015, which hereby claims the benefit of and priority thereto under 35 U.S.C. §§ 119, 120, 363, 365, and 37 C.F.R. § 1.55 and § 1.78, which is incorporated herein by reference, and U.S. patent application Ser. No. 14/795,570 claims benefit of and priority to U.S. Provisional Application Ser. No. 62/022,497, filed Jul. 9, 2014 and is also incorporated herein by this reference.

GOVERNMENT RIGHTS

The subject matter described herein was developed in connection with funding provided by the National Institute of Health (NIH) under Grant No. 5R44CA117218-04 and NIH contract No. HHSN261201400060. The Federal government has rights in the technology.

FIELD OF THE INVENTION

The invention relates generally to an apparatus and method for optical coherence tomography ("OCT") imaging for assessment of interstitial tissue. More particularly, OCT images of the interstitial tissue are taken as a needle including an optical probe is moved within the tissue.

BACKGROUND

Optical coherence tomography (OCT) can be viewed as an optical analog to ultrasound for capturing micrometer-resolution, three-dimensional images from within optical scattering media (e.g., biological tissue). OCT is an interferometric technique that typically employs near-infrared light. OCT typically uses relatively long wavelength light that allows the light to penetrate into a scattering medium. OCT is based on low coherence interferometry.

During OCT imaging, light from a broad band light source (e.g., superluminescent diode) can split between two arms of an interferometer, a sample arm that contains an item of interest and a reference arm (e.g., a mirror). The combination of reflected light from the sample arm and reference light from the reference arm can yield an interference pattern when the interferometer arms are substantially matched within the coherence length of the light source.

OCT imaging can be used to noninvasively or minimally invasively visualize sample morphology on the micron scale. OCT imaging at the micron scale level typically requires the use of a high fidelity scan, where the sample arm light beam of an interferometer is scanned with high linearity (e.g., over 99%) across the sample. However, when the imaging has to be done with a needle size probe that passes through several mm to several cm of an interstitial sample (e.g., tissue), the generation of high linearity scan can require the use of rotary or axial movement of the probe within the tissue, which becomes problematic due to tissue friction.

High-resolution OCT imaging of non-interstitial tissue can require the use of a closed-loop linear scanning engine to scan an optical beam across the tissue and generate a two-dimensional map (e.g., a cross sectional image in the OCT mode and a single dimension map in the spectroscopy mode). Minimally invasive high-resolution OCT imaging of epithelial tissue usually requires the use of a high-speed axial or rotary scanning engine to which the minimally invasive OCT probe is attached. Each of these techniques can prove difficult when imaging interstitial tissue. High-speed and/or rotational movement of an imaging probe in interstitial tissue can cause tissue morbidity by, for example, catching and/or dislocating the tissue, and thus also degrading the linearity of the scan. More recently, scanning mechanisms are being used at the tip of the catheter. However, the size of the scan is limited to a few mm or less, and therefore is not practical for imaging large size areas within the tissue. In addition, the diameter of the catheter is on the order of at least 1 mm and the scanning mechanism cannot be in direct contact with the tissue.

One possible solution to address tissue morbidity and scanning linearity is to place a protective tube over the imaging probe and move the probe inside of it. However, a protective tube typically cannot be pushed to penetrate the tissue. In addition, it increases the overall diameter of a probe, and thus cannot be passed through be 19 gauge or smaller diameter biopsy guidance needles.

A possible solution to minimize tissue disruption and reduce morbidity is to use a manually controlled OCT imaging probe with a sharp tip, similar to a biopsy needle. In this way an operator can maneuver the probe slowly through the tissue in a manner that is less disturbing to the tissue. Scanning linearity however still remains a serious issue. Hand-held OCT imaging devices can suffer from inaccurate imaging due to high nonlinearity of the manual scan. One approach to correct the distortion of the OCT image is to use a computational algorithm (e.g., a speckle model to the OCT decorrelation function to explicitly correlate a cross-correlation coefficient (XCC) to a lateral displacement between OCT A-scans). However, this approach is computationally intensive and is not realistic for real-time correction of images.

Thus, it is desirable for high-resolution OCT imaging of interstitial tissue that both scans nonlinearity and accounts for tissue morbidity.

SUMMARY OF THE INVENTION

One advantage of the invention is that is allows for high-resolution OCT imaging of interstitial tissue by correcting for the nonlinearity of the manual scans and for the distortion of the image caused by tissue noncompliance when the probe is passed through it. Another advantage of the invention is that it provides minimally invasive OCT imaging a minimal tissue disruption due to the operator controlling the position of an optical probe within the interstitial tissue.

Another advantage of the invention is that it does not require probes that are rotated at a high speed and/or moved axially at a high speed to generate high fidelity OCT images. Another advantage is that the low speed scanning enables the recording of high yield co-registered OCT/spectroscopy images. The reasonable integration times (e.g., tens to hundreds of ms) can be used for each imaging voxel, and thus to collect sufficient photons and generate such images. The elimination of the high speed rotation/movement requirements can also allow the use low cost disposable probes.

Another advantage of the invention is that is allows for tissue mapping over relatively long distances (e.g., up to several centimeters), due to the fact that a scanning engine is no longer needed. The interventional radiologist passes the probe through the investigated tissue mass, and the OCT image of the entire trajectory of the probe can be recorded in real-time and conveyed to the operator. Another advantage of the invention is that it can capture a high-resolution OCT image independent of scanning speed. Another advantage of the invention is ease of repeating a procedure because manual positioning of the probe allows for the procedure to be repeated several times without removing the probe from the tissue.

Another advantage of the invention is that it allows for fluorescence imaging or spectroscopy imaging synchronously with OCT imaging due to the elimination of the need for high speed movement to capture an OCT image.

In one aspect, the invention involves a method of imaging a sample. The method involves inserting a guidance needle and an optical probe into an investigation site of the sample, the optical probe being positioned within the guidance needle. The method also involves establishing, using a position sensor, a reference location of the optical probe at a first spatial position at the investigation site relative to the guidance needle. The method also involves capturing a first optical coherence tomography (OCT) A-line with the optical probe at the first spatial position when the optical probe is moved relative to the reference location. The method also involves detecting, using the position sensor, a spatial location of the optical probe relative to the reference location during movement of the optical probe within the sample. The method also involves capturing an OCT A-line with the optical probe at a second spatial position if the reference location and the spatial location are separated by greater than a predetermined threshold value. The method also involves if the second OCT A-line is captured, determining whether the second OCT A-line is identical to the first OCT A-line and discarding the second OCT A-line if it is identical to the first OCT A-line and storing the second OCT A-line and the first OCT A-line if the second OCT A-line and the first OCT A-line are not identical.

In some embodiments, the method involves detecting, using the position sensor, a second spatial location of the optical probe relative to the reference location when the optical probe is moved relative to the reference location. The method also involves capturing an OCT A-line with the optical probe in a third spatial position if the second spatial location and the first spatial location are separated by greater than the predetermined threshold value. If the third OCT A-line is captured, determining whether the third OCT A-line is identical to the second OCT A-line then discarding the third OCT A-line if it is identical to the second OCT A-line, and storing the second OCT A-line and the first OCT A-line if the second OCT A-line and the first OCT A-line are not identical.

In some embodiments, the method involves generating an aggregate OCT image comprising the first OCT A-line and each OCT A-line of the second OCT A-line, the third OCT and any subsequent A-lines for subsequent spatial position OCT A-line that are not a repeat. In some embodiments, maneuvering the optical probe further comprises control by a person, a robot, or any combination thereof. In some embodiments, the second OCT A-line is a repeat of the first OCT image if each A-scan line is substantially similar.

In some embodiments, the aggregate OCT image is a cross-sectional OCT image. In some embodiments, the method involves emitting light from the optical probe that has a wavelength of approximately 1310 nanometers or approximately 1060 nanometers with a bandwidth of between 10 nanometers and 100 nanometers. In some embodiments, a fluorescence image or a spectroscopy data set is spatially co-registered with the OCT image.

In another aspect, the invention includes a hand-held optical coherence tomography (OCT) sample imaging system. The system also includes an optical probe positioned and movable within a guidance needle, the optical probe capable of capturing OCT A-lines of the sample. The system also includes an optical scale coupled to the optical probe. The system also includes a position sensor spatially positioned relative to the optical scale, the position sensor configured to detect a location of the optical probe relative to the guidance needle for each OCT A-line taken during imaging, the detection is based on the location of the optical scale. The system also includes a processing unit in communication with the optical probe is configured to record and display cross-sectional OCT images of the sample.

In some embodiments, the system also includes a fluorescence or spectroscopy unit coupled to the optical probe configured to record a spatially co-registered fluorescence image or spectroscopy data set with the OCT image. In some embodiments, the processing unit is configured to determine whether a first OCT A-line taken at a first spatial location is a repeat of a second OCT A-line taken at a second spatial location, and generate an aggregate OCT image comprising the first OCT A-line and the second OCT image if the second OCT A-line and subsequent OCT A-lines are not a repeat.

In some embodiments, the reference point is the handle or the guidance needle. In some embodiments, the system also includes a person, a robot or any combination thereof, maneuvers the optical probe by manipulating the hand-held unit. In some embodiments, the system also includes the second OCT A-line is a repeat of the first OCT A-line if each A-line is substantially identical.

In some embodiments, the system also includes the optical probe emits light that has a wavelength of approximately 1310 nanometers or approximately 1060 nanometers with a bandwidth of between 10 nanometers and 100 nanometers. In some embodiments, the system also includes the aggregate OCT image is a cross-sectional OCT image. In some embodiments, the system also includes an optical scale coupled to the optical probe.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

Generally, an apparatus including an optical probe capable of taking an OCT image is inserted into interstitial tissue. The optical probe is manually moved (e.g., by a technician or a robot). When the optical probe is moved more than approximately 5 microns from a reference point (e.g., a guidance needle or a handle), an OCT reflectivity profile or A-line is taken. Each OCT A-line is analyzed by a data processor to determine whether or not it is a repeat of the previous A-line. Repeated A-lines are discarded. The data process presents an aggregate OCT image of the interstitial tissue based on each non-discarded OCT A-line.

Figure 1:
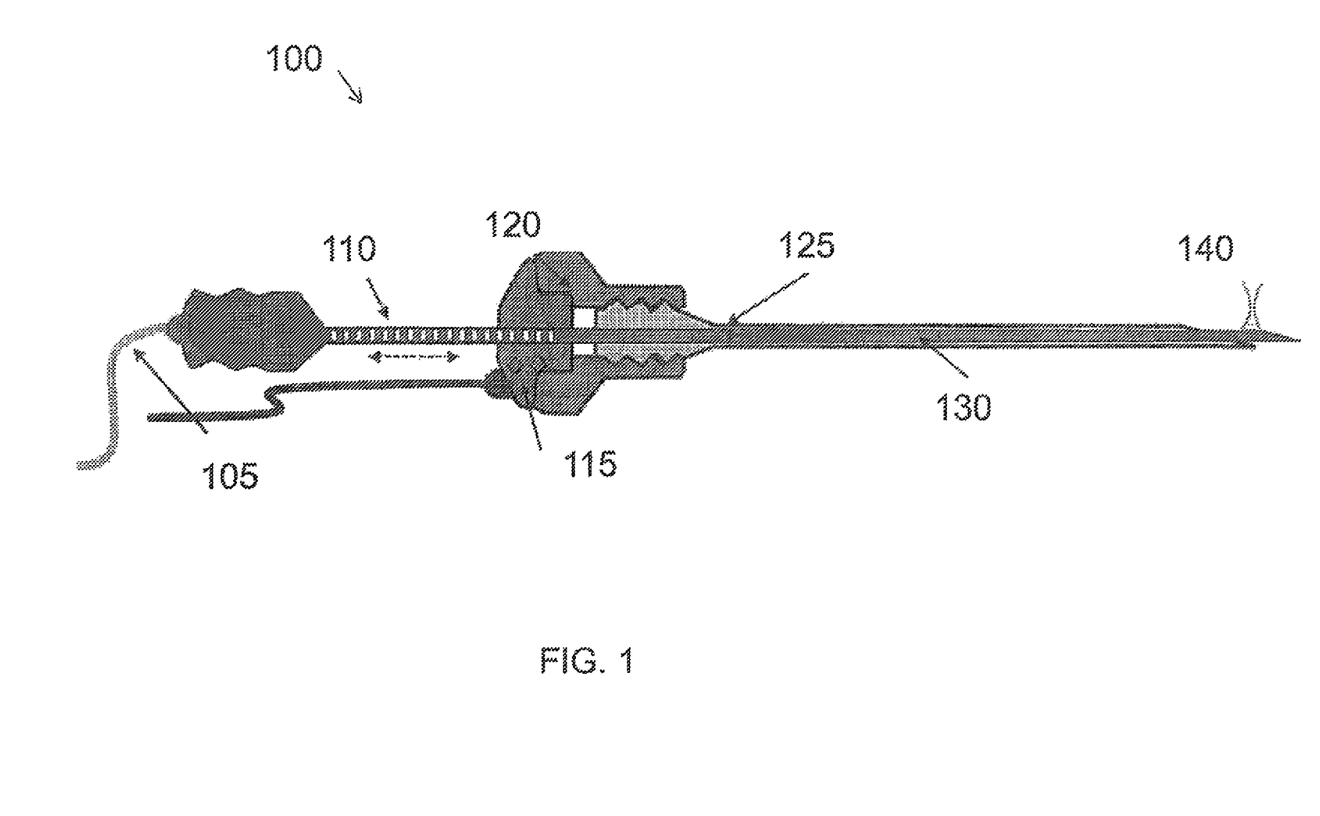
FIG. 1 is a diagram of a hand-held optical imaging probe, according to an illustrative embodiment of the invention.

FIG. 1 is a diagram of a hand-held optical imaging device 100, according to an illustrative embodiment of the invention. The hand-held optical imaging device 100 includes an optical fiber 105, an optical scale 110, a position sensor 115 (e.g., optical encoder), a connector 120 (e.g., male luerlock connector), a guidance needle 125, and an optical probe 130 encapsulated into a hypodermic tube with a sharp tip. When in use, the hand-held OCT imaging device 100 emits a light beam 140.

The connector 120 is coupled to the guidance needle 125. The guidance needle 125 has the optical probe 130 disposed therein. The optical probe 130 passes through the connector 120 and has attached or engraved an optical scale 110. The optical encoder 115 is coupled to the connector 120 at a location that allows the optical encoder 115 to detect a change in position of the optical scale 110.

The optical fiber 105 is coupled to the optical probe and connects it to an optical imaging instrument (not shown).

In some embodiments, the optical probe 130 is a single mode (SM) OCT fiber probe that is terminated with a side looking micro-objective lens. In various embodiments, the optical probe 130 is a combined OCT/fluorescence or absorption/Raman spectroscopy probe, which utilizes either a double clad fiber to collect the fluorescence or absorption/Raman spectroscopy signal, or a separate fiber adjacent to the OCT fiber. In some embodiments, the guidance needle 125 is a transcutaneous biopsy needle. In some embodiments, the guidance needle 125 is up to several inches in length (e.g., 3 to 15 inches). In some embodiments, the guidance needle 125 is a long biopsy needle (e.g., 4 to 6 feet in length), used in conjunction with GI endoscopes, being delivered inside the body through the instrument channel of such endoscopes.

During operation, the guidance needle 125 is first inserted into the interstitial sample (e.g., kidney, heart, lungs, liver, etc., of a patient) by an operator. Ultrasound or CT guidance can be used for correct placement of the transcutaneous biopsy needles within the tissue location to be examined, while endoscopy guidance is used for proper placement of long needles.

The operator inserts the optical probe 130 through the guidance needle 125 until the tip of the optical probe 130 outreaches the tip of the guidance needle 130 to a position sufficient to send the imaging beam to the interstitial tissue (e.g., 2-5 mm). Once in a desired position, the operator can maneuver only the optical probe 130 to extend further into the interstitial tissue, while the guidance needle 125 remains substantially unmoved.

The optical encoder 115 detects any incremental movement of the optical scale 110. When the optical encoder 115 detects that the location of the optical probe 130 moves more than a predetermined threshold (e.g., 5 microns or more), the optical encoder 115 generates a trigger signal that is transmitted to an OCT spectrometer camera (not shown). In some embodiments, the predetermined threshold is a function of the resolution of the encoder/scale assembly.

The trigger signal instructs the OCT spectrometer camera to take a signal (e.g., record an OCT reflectivity profile or A-line). An operator maneuvering the optical probe 130 can move as quickly or as slowly as is needed (e.g., for comfort of the patient) because the triggering event for taking an OCT image can be based on location and not time.

For each OCT A-line taken, the data processor compares the image with a previous OCT A-line taken. If the A-lines are substantially the same, then the data processor discards the repeated A-lines. An aggregate OCT image (e.g., a tomographic OCT image or cross-sectional) is compiled based on all non-repeat A-lines. In this manner, if the optical probe 130 is stuck within the interstitial tissue such that the interstitial tissue moves with the optical probe 130, a correction is made to discard the repeat voxels from the image. The aggregate OCT image can be displayed in real-time.

In some embodiments, the predetermined threshold is based on desired imaging resolution, usually 5 to 25 microns. In some embodiments, the optical scale 110 is an engraved optical scale. In some other embodiments, the optical scale 110 is an attached scale. An attached scale can allow the optical probe to be disposable with a low cost.

In some embodiments, the optical probe 130 is between 300 and 2000 microns in diameter. In some embodiments, the optical probe 130 diameter depends on the size and the length of the biopsy guidance needle. In some embodiments, the optical probe 130 is a regular single mode (SM) fiber that is optic-based. In some embodiments, the optical probe 130 is a combination of a SM fiber and a multimode (MM) fiber, the SM being used for OCT imaging and the MM used for fluorescence or spectroscope. In some embodiments, the optical probe 130 is a dual clad fiber where the core is used for OCT and spectroscopy or fluorescence illumination, and the 2nd clad for collecting the fluorescence or spectroscopy photons.

Figure 2:
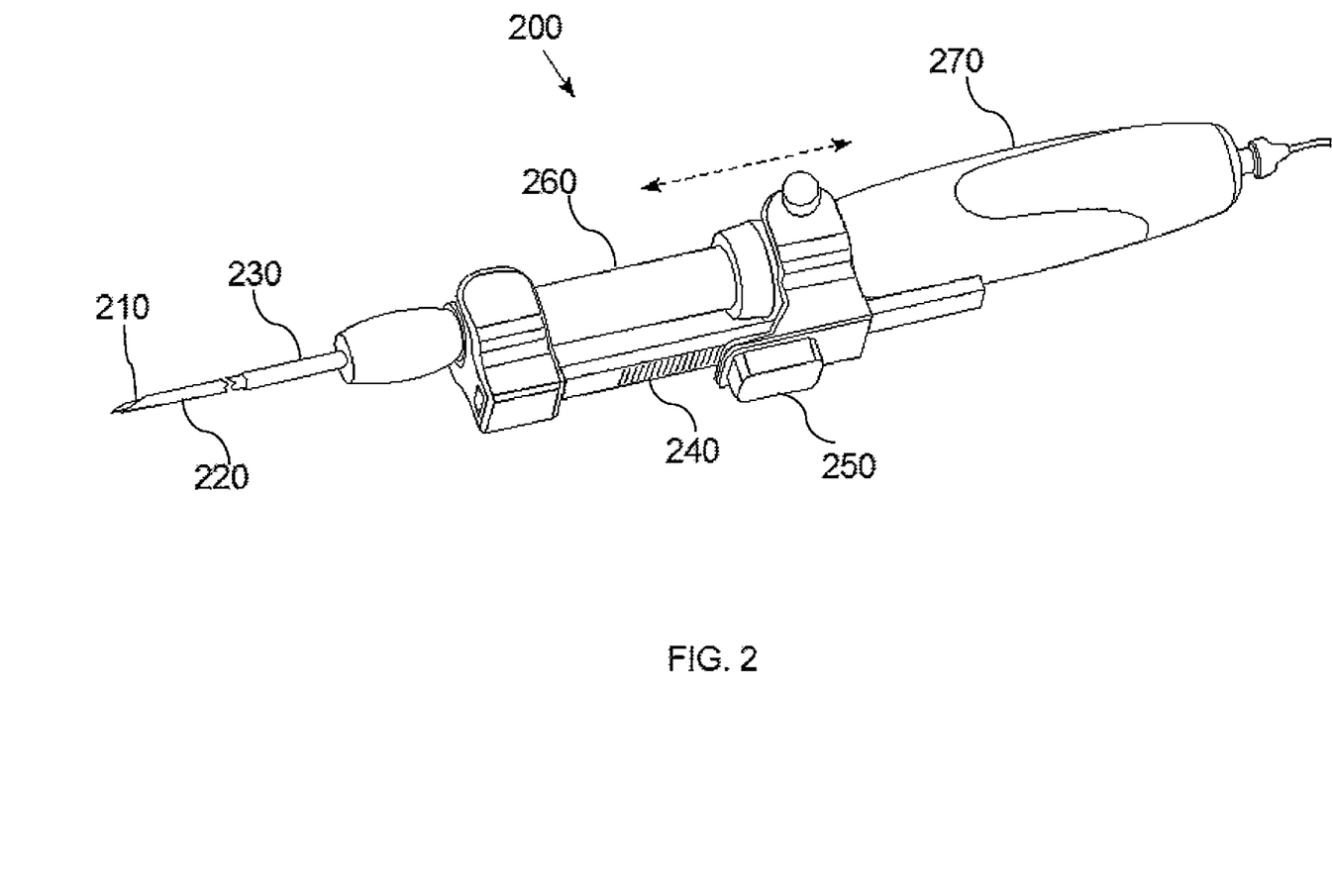
FIG. 2 is a diagram of a hand-held optical probe, according to an illustrative embodiment of the invention.

FIG. 2 is a diagram of a hand-held OCT imaging device 200, according to an illustrative embodiment of the invention. The hand-held OCT imaging device 200 includes an optical probe 210, a biopsy needle 220, a jacket 230, an optical scale 240, an encoder 250, a holder 260 and a handle 270.

The optical probe 210 is positioned within the biopsy needle 220. The biopsy needle is positioned within a jacket 230. The jacket 230 is coupled to the holder 260. The holder 260 is coupled to the optical scale 240. The holder 260 is coupled to the handle 270. The handle 270 is coupled to the encoder 250.

During operation, the biopsy needle 220 with a stilet disposed therein (not shown) is placed within the interstitial tissue of interest under endoscopic guidance. The stilet is removed and the optical probe 210 is inserted into the biopsy needle 220 until it reaches the interstitial tissue (e.g., a pancreas, stomach, or other organ of interest). The optical probe 210 is locked to the biopsy needle 220, so that the optical probe 210 and the biopsy needle 220 can move together when the handle 270 is moved. The biopsy needle 220 is maneuvered by a person (or a robot) manipulating the handle 270.

When the handle 270 is moved forward, the biopsy needle 220 and the optical probe 210 are moved forward. The encoder 250 attached to the handle 270 moves relative to the optical scale 240, which is attached to the holder 260. Therefore, any movement of the optical probe 210 inside the tissue is monitored by the encoder 250, which generates trigger pulses and starts the acquisition of the OCT A-lines.

Figure 3:
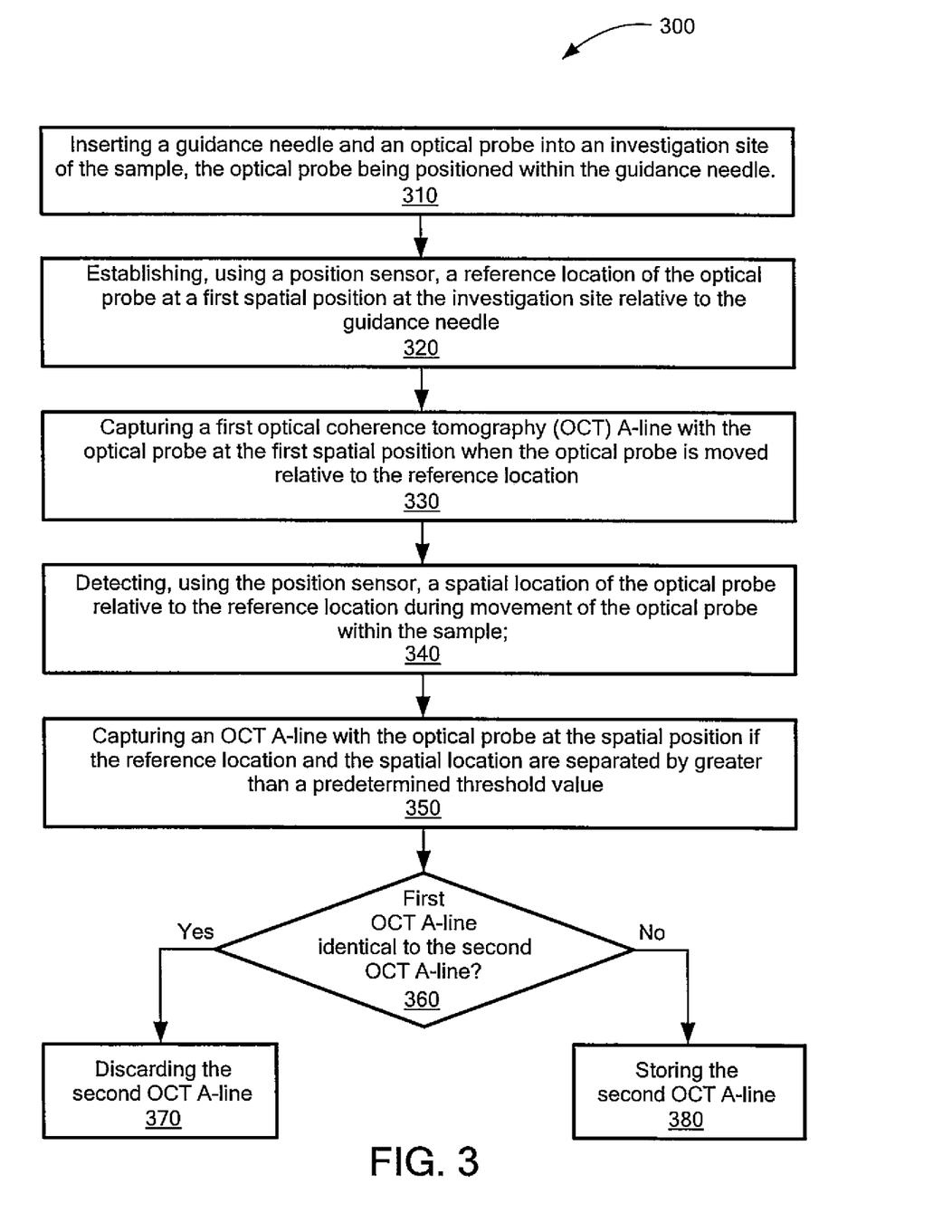
FIG. 3 is a flow chart of a method for interstitial tissue OCT imaging and biopsy guidance, according to an illustrative embodiment of the invention.

FIG. 3 is a flow chart of a method 300 for sample OCT imaging and biopsy guidance, according to an illustrative embodiment of the invention. The method involves inserting a guidance needle (e.g., guidance needle 125 as shown above in FIG. 1) and an optical probe (e.g. interstitial sample (Step 310), the optical probe being positioned within the guidance needle. In some embodiments, the guidance needle is inserted into the sample with a stilet, the stilet is removed and then the optical probe is inserted. In some embodiments, the guidance needle and the optical probe are coupled prior to insertion.

The sample can be any tissue of a mammal that needs to be investigated or any biological/non-biological specimen. The investigation site, in a mammal, can be a site of interest having some shape and size defined by previous radiological or ultrasound imaging, or by real-time radiological or ultrasound imaging. For example, for a patient that previously had cancer (e.g., breast cancer), the investigation site can be well defined area having a different radiological appearance than the surrounding tissue. In some embodiments, the investigation site is based on the images (e.g., Ct or ultrasound) taken during the investigation (e.g., biopsy procedure). The optical probe can be an OCT imaging probe.

The method also involves establishing, using a position sensor, a reference location of the optical probe at a first spatial position at the investigation site relative to the guidance needle (Step 320).

The method also involves capturing a first optical coherence tomography (OCT) A-line with the optical probe at the first spatial position when the optical probe is moved relative to the reference location (Step 330).

The method also involves detecting, using the position sensor, a spatial location of the optical probe relative to the reference location during movement of the optical probe within the sample (Step 340). The position sensor can be an optical encoder, a magnetic position sensor, or any position sensor as is known in the art.

The method also involves capturing an OCT A-line with the optical probe at a second spatial position if the reference location and the spatial location are separated by greater than a predetermined threshold value (Step 350). In some embodiments, the predefined threshold value is 5 microns. In various embodiments, the predefined threshold value is between 1 and 25 microns.

The method also involves determining whether the second OCT A-line is identical to the first OCT A-line (Step 360). In some embodiments, the determination as to whether the first and second OCT A-lines are the same is based on the following:

If $I_{Axi+1} - I_{Axi} > k$, then $A_{xi+1} = 0$     (EQN. 1)

Where $I_{Ax}$ is intensity of each pixel from successive A line of the first OCT image, $I_{Axi+1}$ is intensity of each pixel from successive A line of the second OCT image, and k is a threshold constant. In various embodiments, k is an experimentally established threshold based on image intensity, or is automatically determined by the OCT processor.

If the first OCT A-line and the second OCT A-line are identical then the second OCT A-line is discarded (Step 370). If the first OCT A-line and the second OCT A-line are not identical the first OCT A-line and the second OCT A-line are stored (Step 380). The first OCT A-line and the second OCT A-line can be stored in an array.

In this manner, at periodic intervals, an OCT A-line image is taken each time the optical probe moves beyond the predetermined threshold. For each A-line image that is taken, if it is not identical to the previous A-line image, then it is stored in the array. The array can be used by the processor to append all of the non-discarded A-lines into one cohesive OCT image.

In some embodiments, the imaging probe is a combined OCT/fluorescence or OCT/Spectroscopy image. The Fluorescence or spectroscopy data can be used in conjunction with the OCT data to provide enhanced differentiation of tissue nature (e.g., normal, solid tumor, heterogeneous tissue, necrotic tissue). Either the operator or an automated tissue differentiation algorithm can be used to determine tissue nature in real time.

In some embodiments, the probe is reoriented into a different spatial location of the tissue, e.g., if the investigated location by OCT or combined OCT/fluorescence/spectroscopy does not show a correlation with the radiological finding. In these embodiments, the optical probe can be manually retracted until it reaches the tip of the biopsy guidance needle and the needle optical probe assembly can be reoriented to a different position or angle to reach a different area of the investigated tissue (350) to collect a new data set.

If used for biopsy guidance, the procedure can be repeated several times until the operator determines, based on the collected data, that a specific location within the tissue specimen is the right one to collect a tissue specimen. Then, the optical probe is retracted and the biopsy cutting needle is inserted through the guidance needle to collect a tissue specimen (biopsy core or an assembly of cells and fluid (for aspiration biopsies).

Figure 4:
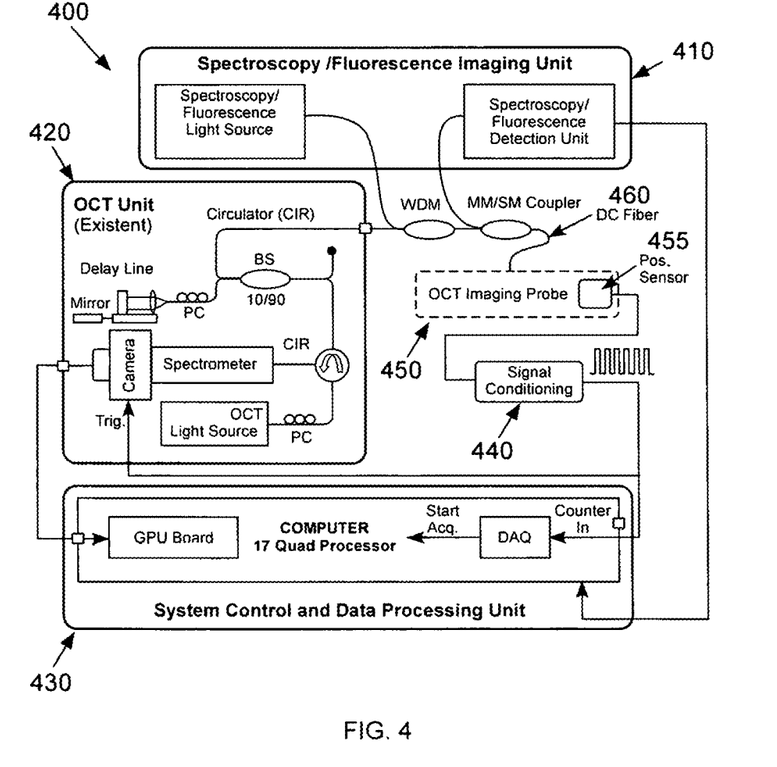
FIG. 4 is a schematic of a system combined OCT/spectroscopy or OCT/Fluorescence imaging that includes the connection to a hand-held optical imaging device, according to an illustrative embodiment of the invention.

FIG. 4 is a schematic of a system 400 for OCT imaging includes a hand-held OCT imaging device, according to an illustrative embodiment of the invention.

The system 400 includes a spectroscopy/fluorescence imaging unit 410, an OCT unit 420, a system control and data processing unit 430, a signal conditioner 440, an OCT imaging probe 450 that includes a position sensor 455 and a division multiplexing fiber component 460.

The spectroscopy/fluorescent imaging unit 410 and the OCT unit 420 are in communication with the OCT imaging probe 450 through the division multiplexing fiber component 460. The spectroscopy/fluorescent imaging unit 410 and the OCT unit 420 are also in communication with the system control and data processing unit 430. The system control and data processing unit 430 is also in communication with the OCT imaging probe 450 via the signal conditioning unit 440.

During operation, the OCT imaging probe 450 is inserted into interstitial tissue. The position sensor 455 detects the position of the probe in the interstitial tissue during imaging.

The signal conditioning unit 440 receives the imaging data and minimizes noise on the received data and/or instructs the system control and data processing unit 430 to start acquisition of the signals. The system control and data processing unit uses the position data from the position sensor 455 to append the consecutive signals to an array and form a cross-sectional OCT image. It also determines whether consecutive A-lines are repeats or new A-lines of an investigation site of the interstitial tissue (e.g., for example, by using method 300).

The spectroscopy/fluorescence imaging unit 410 transmits/receives signals from the imaging probe that can be used in correlation with the OCT image to improve tissue discrimination. The wavelength can be between 400 and 800 nanometers.

Figure 5:
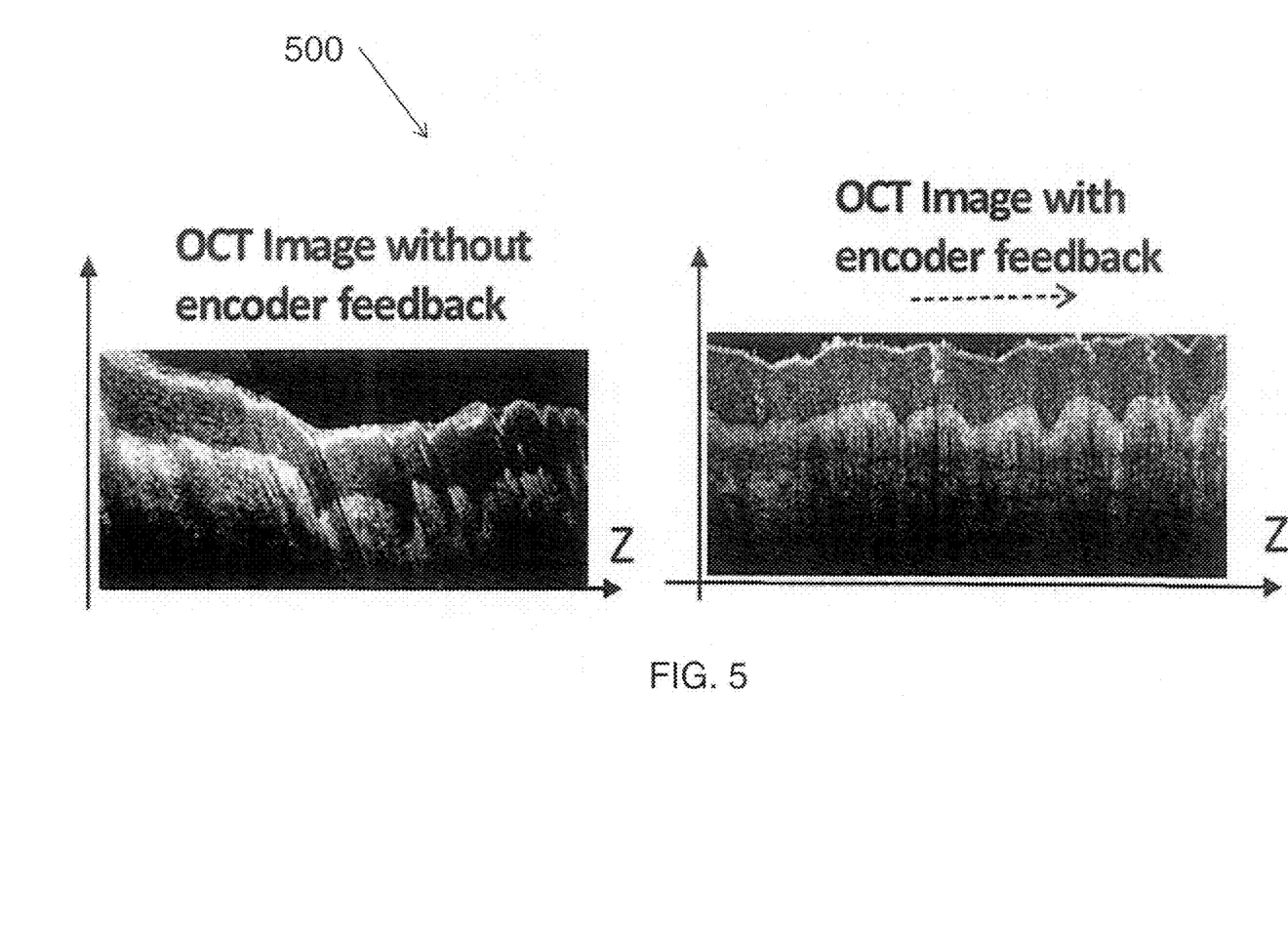
FIG. 5 is a graph showing a comparison of OCT images of interstitial tissue with and without encoder correction, according to an illustrative embodiment of the invention.

FIG. 5 is a graph 500 showing a comparison of OCT images of interstitial tissue with and without correction, according to an illustrative embodiment of the invention. The image with encoder feedback represents a distorted image of the tissue true morphology, while the one with encoder feedback represents the true morphology of the tissue.

Figure 6:
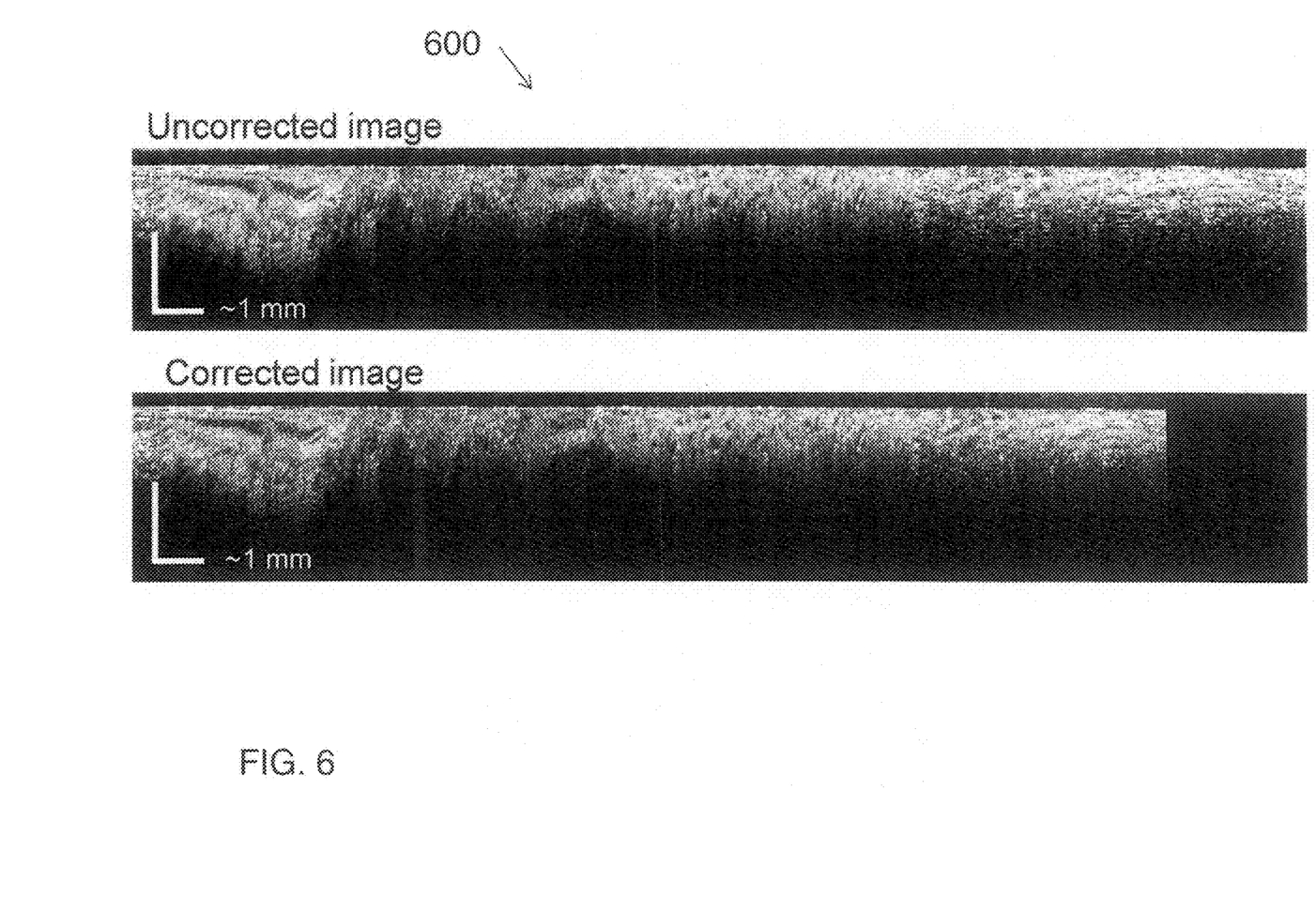
FIG. 6 is a graph showing a comparison of OCT images of interstitial tissue with and without corrections, according to an illustrative embodiment of the invention.

FIG. 6 is a graph 600 showing a comparison of OCT images of interstitial tissue, according to an illustrative embodiment of the invention. As observed the repeated voxels from the uncorrected image are eliminated from the corrected image, which is physically shorter and represents the true morphology of the tissue.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

Other embodiments will occur to those skilled in the art and are within the following claims.

What is claimed is:

1. A hand-held optical coherence tomography (OCT) system for sample imaging comprising:
    an optical probe positioned and movable within a guidance needle configured to be inserted into the sample;
    an optical scale on the optical probe;
    a position sensor spatially positioned relative to the optical scale, the position sensor and the optical scale configured to detect linear movement of the optical probe relative to the guidance needle by more than a predetermined amount and in response generating a trigger signal to record an OCT A-line of the sample at every incremental movement of the optical probe more than said predetermined amount;
    a processor unit responsive to the trigger signal and configured to store the OCT A-line each time the optical probe moves relative to the guidance needle tip by more than said predetermined amount and to append said OCT A-lines recorded at different positions into a data array used to form a cross-sectional OCT image of the sample.

2. The system of claim 1 in which a processing unit is further configured to record said OCT A-lines and display said cross-sectional OCT image of the sample only when triggered by the position sensor trigger signal.

3. The system of claim 2 wherein the processing unit is configured to:
    determine whether a second OCT A-line of said OCT A-lines is a repeat of a first OCT A-line of said OCT A-lines,
    and generate the cross-sectional OCT image comprising the first OCT A-line and the second OCT A-line if the second OCT A-line is nota repeat of the first OCT A-line.

4. The system of claim 1 further comprising a fluorescence unit or spectroscopy unit coupled to the optical probe configured to record a spatially co-registered fluorescence image or spectroscopy data set with the cross-sectional OCT image.

5. The system of claim 1 wherein the optical probe is capable of being maneuvered manually.

6. The system of claim 1 in which the optical probe emits light that has a wavelength of 1310 nanometers or 1060 nanometers with a bandwidth of between 10 nanometers and 100 nanometers.

7. A hand-held optical coherence tomography (OCT) sample imaging system comprising:
    an optical probe positioned and movable within a guidance needle;
    an optical scale placed on the optical probe;
    a position sensor spatially positioned relative to the optical scale, the optical scale and the position sensor configured to detect linear movement of the optical probe relative to the guidance needle; and
    a processing unit in communication with the optical probe and responsive to the position sensor and configured to record and display a cross-sectional OCT image of a sample by:
    determining, in response to a signal output by the position sensor, if the optical probe has moved relative to the guidance needle by a predetermined distance;
    capturing a first OCT A-line only when the optical probe is moved by the predetermined distance,
    capturing a second OCT A-line when the optical probe is again moved by the predetermined distance,
    determining whether the second OCT A-line is substantially identical to the first OCT A-line,
    discarding the second OCT A-line if it is substantially identical to the first OCT A-line, and
    storing the second OCT A-line and the first OCT A-line if the second OCT A-line and the first OCT A-line are not substantially identical.

8. The system of claim 7 further comprising a fluorescence unit or spectroscopy unit coupled to the optical probe and configured to record a spatially co- registered fluorescence image or spectroscopy data set with the cross-sectional OCT image.

9. The system of claim 7, wherein the optical probe is capable of being manually maneuvered.

10. The system of claim 7 in which the optical probe emits light that has a wavelength of 1310 nanometers or 1060 nanometers with a bandwidth of between 10 nanometers and 100 nanometers.

* * * * *